United States Patent [19]

Sipos

[11] Patent Number: 5,614,223
[45] Date of Patent: Mar. 25, 1997

[54] INTRAORAL MEDICAMENT-RELEASING DEVICE

[75] Inventor: Tibor Sipos, Lebanon, N.J.

[73] Assignee: Digestive Care Inc., Lebanon, N.J.

[21] Appl. No.: 503,202

[22] Filed: Jul. 17, 1995

Related U.S. Application Data

[63] Continuation-in-part of Ser. No. 109,632, Aug. 20, 1993, Pat. No. 5,433,952, which is a continuation-in-part of Ser. No. 878,155, May 4, 1992, abandoned.

[51] Int. Cl.$^6$ ........................................................ A61K 9/14
[52] U.S. Cl. ........................... 424/489; 424/435; 424/490; 424/497; 424/486
[58] Field of Search .................................. 424/488, 489, 424/490, 493, 92

[56] References Cited

U.S. PATENT DOCUMENTS

| | | | |
|---|---|---|---|
| 3,624,909 | 12/1971 | Greenberg | 433/80 |
| 3,688,406 | 9/1972 | Porter et al. | 433/217.1 |
| 4,020,558 | 5/1977 | Cournut et al. | 433/80 |
| 4,175,326 | 11/1979 | Goodson | 433/80 |
| 4,661,350 | 4/1987 | Tsurumizu et al. | 424/92 |
| 4,681,544 | 7/1987 | Anthony | 433/215 |
| 4,685,883 | 8/1987 | Jernberg | 433/215 |
| 4,837,030 | 6/1989 | Valorose, Jr. et al. | 424/456 |
| 4,919,939 | 4/1990 | Baker | 424/493 |
| 4,935,411 | 6/1990 | McNamara | 514/152 |

FOREIGN PATENT DOCUMENTS 0184389  6/1986  European Pat. Off. .

OTHER PUBLICATIONS

M. Friedman, Fluoride Uptake by Powdered Human Enamel Treated with Prolonged Active Fluoride Pellets in Vitro, Arch. Oral. Biol. V. 26, pp. 131–134, 1981.
D. Mirth et al, Development and In Vitro Evaluation of an Intra–Oral Controlled–Release Delivery System for Chlorhexidine, J. Dent. Res., Aug. 1989.
Southern Research Institute Bulletin, Winter 1979, V. 32, No. 1, pp. 16–22.
D. Mirth et al, Clinical Evaluation of an Introral Device for the Controlled Release of Fluoride, JADA, V. 105, Nov. 1982, pp. 781–797.
H. K. Morisaki et al, local Ofloxacin Delivery Using a Controlled–Release Insert (PF01) in the Human Periodontal Pocket, J. Periodont. Res. 1990, 25:1:5.
T. Larson, In Vitro Release of Doxycycline from Bioabsorbable Materials and Strips, J. Periodontal Research, 1990; 61; 30–34.

Primary Examiner—Thurman K. Page
Assistant Examiner—William E. Benston, Jr.

[57] ABSTRACT

Disclosed are controlled rate-release devices for releasing a pharmaceutically active agent into the oral cavity by the dissolving action of the saliva, a process of preparing such devices and methods of preventing/treating conditions/diseases in a mammal by delivering a pharmaceutically active substance into the oral cavity.

23 Claims, No Drawings

INTRAORAL MEDICAMENT-RELEASING DEVICE

This application is a continuation-in-part of application Ser. No. 08/109,632, filed on Aug. 20, 1993, U.S. Pat. No. 5,433,952 which in turn is a continuation-in-part of application Ser. No. 07/878,155, filed on May 4, 1992, now abandoned.

BACKGROUND OF THE INVENTION

1. Field of the Invention

This invention relates to intraoral medicament-releasing devices capable of slowly releasing an agent into the oral cavity, to a process of manufacturing such devices, and methods for the prevention and treatment of certain diseases including dental caries, incipient carious lesions and periodontal diseases. More particularly, the invention relates to a controlled rate-release device comprising an inner core containing a pharmaceutically acceptable agent and an outer layer of a saliva-insoluble, non-erodible rate-controlling membrane allowing water to enter into the inner core to dissolve the pharmaceutically acceptable agent which then diffuses through the rate-controlling membrane into the oral environment.

2. Reported Developments

Dental practitioners and their patients are aware of the importance of proper oral hygiene in maintaining healthy teeth and gums. Routine use of toothbrush, toothpaste, fluoride rinse and floss as well as periodic visits to the dentist to remove plaque and calculus from the root surfaces greatly contributes to such oral care maintenance. However, this routine must be kept diligently, and even then, it is only effective to a limited extent regarding certain oral conditions.

Dental caries and periodontal diseases are widespread chronic conditions. Caries is an infectious disease caused by bacteria. Bacteria metabolize fermentable carbohydrates to organic acids. The acids in close contact with the enamel cause enamel demineralization. Extensive demineralization leads to dental caries. Caries may be prevented by the frequent use of fluorides. Fluoride enhances enamel remineralization, increases tooth resistance to further acid attack, and arrest the progression of caries. Fluorides are employed in toothpastes, tablets, drops, mouth rinses and drinking water. Periodontal diseases are inflammatory conditions affecting the tooth supporting structures. Anaerobic bacteria proliferates in the gingival crevice, produce enzymes, toxins and noxious metabolites that accumulate in the gingival crevice. These bacterial by-products are irritating to the gingival tissue and initiate a localized inflammation. The inflamed tissues release enzymes that destroy the collagen supporting fibers and alveolar bone. If this process is left unchecked it will eventually lead to the exfoliation of tooth.

In addition to dental caries and periodontal diseases a certain segment of the population suffers from other ailments and conditions of the oral cavity.

Xerostomia, or dry mouth condition, is frequently caused by a dysfunction of the major salivary glands and is associated with a number of diseases. Xerostomia may also be caused by certain medication especially in the elderly. Radiation treatment of head and neck cancer may also result in xerostomia. Patients who undergo orthodontic treatment for various health and cosmetic reasons that require wearing of orthodontic devices experience white-spot enamel lesions around the orthodontic bands due to accumulation of plaque. Denture wearers experience irritation and painful lesions on the roof of the mouth as a result of which masticatory functions are impaired and the patients also develop digestive problems and nutritional deficiencies. Handicapped individuals are at a greater risk of developing rampant caries because of the physical limitations imposed by their handicaps and good oral hygiene.

Periodontal treatment utilizes mechanical debridement of tooth surfaces and root planning and scaling. Systemically administered antibiotics have also shown some promise as an antimicrobial measure.

These treatments, although effective against bacteria at the time of administration are not sufficiently long-lasting. Bacteria proliferates within hours in the oral cavity and condition leading to caries and periodontal disease reappear again. It is apparent that since these disorders are chronic, the duration of drug presence at the target site is critical in both prevention and therapy.

These conditions and ailments are treatable, since it has been shown that a low level of fluoride which constantly enriches the saliva has the potential to prevent the development of dental caries and associated conditions in the oral cavity. (See O. Fejerskov, A. Thylstrup and M. J. Larsen: Rational Use of Fluorides in Caries Prevention. A Concept Based on Possible Cariostatic Mechanisms. Acta Odontol Scand. 39(4): 241–249 (1981)). Accordingly, a fluoride-containing reservoir which can release fluoride at a constant rate to enrich the saliva with therapeutically effective levels of fluoride is required (See D. B. Mirth and W. H. Bowen. A Microbial Aspect of Dental Caries. Vol. 1 pp. 249–262, Information Retrieval Inc., Washington, D.C. (1976)).

It is also apparent that most of the currently marketed products to prevent rampant caries associated with xerostomia and other oral ailments are deficient for several reasons, such as lack of sustained-release fluoride, adequate patient compliance, unpleasant taste and cumbersomeness of application, lack of control of applied dosage and the potential toxic effect from the product being swallowed accidentally.

Although at present there are no commercially available products on the market based on long term sustained-release, controlled delivery principle, efforts are being made to provide such products as illustrated by the following references.

Slow-releasing devices to be attached to or placed around teeth or implanted into the gum are disclosed, for example, in U.S. Pat. Nos. 3,624,909; 3,688,406; 4,020,558; 4,175,326; 4,681,544, 4,685,883, 4,837,030 and 4,919,939. While these devices do deliver a medication into the oral cavity, they lack a controlled rate of delivery for extended time periods which is of utmost importance in the prevention and treatment of the heretofore mentioned diseases and conditions. For example, U.S. Pat. No. 4,837,030 discloses an orally administrable pharmaceutical composition comprising beads coated with an ultrathin layer of a polymer that erodes under gastric conditions. When suspended in water, more than 90% of the pharmaceutical agent is released from the composition between 20 to 90 minutes; U.S. Pat. No. 4,919,939 discloses a controlled release drug delivery system comprising a polymeric matrix which dissolves, releasing the drug contained therein within 10 to 18 hours, upon the action of the saliva.

Polymeric varnishes containing the antiseptic chlorhexidine or cetylpyridinium in ethylcellulose or polyurethane varnishes were found to be effective to prevent plaque formation. However, the antibacterial effects are short-term and the application of the varnishes has to be repeatedly performed by a dentist.

Hollow fibers and methacrylate slabs containing antibacterial agents, such as tetracycline, placed into periodontal pockets were also found effective. Lack of esthetics, pain and discomfort caused by such devices limit their use to only certain patients with extreme cases of periodontal disease.

A device for attachment to teeth and to deliver sodium fluoride or chlorhexidine at a controlled-rate was found effective in delivering the active substances at a constant linear rate. The device comprises a copolymer hydrogel of hydroxyethyl methacrylate and methyl methacrylate as the inner core which holds the active agents, while the outer layer, a copolymer of the same constituents at a different mole ratio controls the drug release rates. See D. B. Mirth et al, Development and In Vitro Evaluation of an Intra-Oral Controlled-Release Delivery System for Chlorhexidine, J. Dent. Res. August (1989); D. B. Mirth et al, Clinical Evaluation of an Intraoral Device for the Controlled Release of Fluoride, JADA, Vol. 105, November (1982).

While this system of delivery is excellent for fluoride and chlorhexidine, there is no process or method disclosed by which the device could be manufactured economically. Laboratory scale or hand-made small size devices of this type tend to be prohibitively expensive and unaffordable by that segment of the public which needs it the most. Also, there is no provision disclosed to tailor-make the device to deliver fluorides or chlorhexidine so that prophylactic or treatment requirements of patients could be satisfied allowing for different rates and duration of delivery. Furthermore, no process is taught by which uniform and predictable dosage could be assured.

Analogous to the controlled rate-release device for the prevention and treatment of dental diseases, the device of the present invention may be used for the prevention and treatment of other diseases which require slow and controlled rate-release of a pharmaceutically active agent. Such diseases include impotency, osteoporosis, tumors, drug abuse, yeast infection and the like. While slow release devices are well known and successfully utilized by the pharmaceutical industry in the form of topical dressings, such as wound and burn dressing, intra-oral devices proposed for long term delivery of drugs are few and provide insufficient duration of delivery at a constant rate. Typically, such devices, while capable of delivering medicaments, such as psychotropic agents, antispasmodics, anti-inflammatory agents, hormones, antibiotics and the like, deliver their active agents within ours or within a couple of days after their introduction into the oral cavity. An example of such devices is disclosed in U.S. Pat. No. 4,876,092.

The present invention solves these and other problems as will be discussed as the description of the invention proceeds.

SUMMARY OF THE INVENTION

The present invention relates to a slow, controlled rate release device which is provided for releasing a pharmaceutically acceptable active agent into the oral cavity by the hydrating action of the saliva comprising:

(a) a pharmaceutically acceptable active agent releasing core comprising from about 1 to about 84% w/w of said active agent; and from about 35 to about 15% w/w of 2-hydroxy ethyl methacrylate/methyl methacrylate copolymer (hereinafter HEMA:MMA) which comprises from about 40 to about 60 mole % HEMA and from about 60 to about 40 mole % MMA; and (b) a release rate controlling membrane forming copolymer coating uniformly covering said core, which coating comprises from about 10 to about 40 mole % HEMA and from about 60 to about 90 mole % MMA at a coating thickness proportional to the desired rate of release of the active agent from said core.

The pharmaceutically active agent utilized in the present invention includes, but is not limited to: testosterone; calcitonin; octreotide aqcetate; cholecystokinin (CCK); C-terminal octapeptide of cholecystokinin (CCK-8); derivatives of CCK-8 such as N-sarkosyl-CCK-8; N-taurine-CCK-8; N-pyroglutamic-CCK-8; C-terminal heptapeptide of CCK (CCK-7); N-sarkosyl-CCK-7; N-taurine-CCK-7; N-pyroglutamic-CCK-7; t-BOCK-CCK-7; methadone hydrochloride; nystatin; fluoride ion releasing substances, such as sodium fluoride, calcium fluoride, amine fluoride, sodium monofluorophosphate and stannous fluoride; antibiotic tetracyclines, such as doxycycline and minocycline (Minocin, Achromycin and Vibramycin); anti-collagenolytic tetracyclines, such as 4,4-dedimethylaminotetracycline; 4-hydroxy-4-dedimethylamino tetracycline, tetracycline-2-hydroxamate and other chemically modified non-antimicrobial tetracycline; anti-microbials, such as chlorhexidine, cetylpyridinium and metronidazole; salivary stimulants, such as pilocarpin; and mouth deodorants, such as alpha and beta ionones.

The pharmaceutically active agents utilized by the present invention are commercially available from pharmaceutical companies or they can be prepared utilizing known preparative processes and ingredients. For example: C-terminal octapeptide of cholecystokinin having the formula

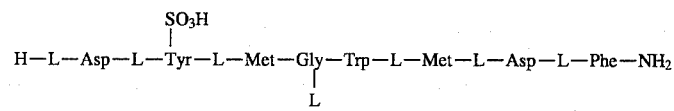

is available from Squibb Hospital Division in New Jersey while cholecystokinins and its analogs are available from Research Plus, Inc. of Bayonne, N.J.; Nystatin is available from Bristol-Myers; and Calcitonin is available from Rhone-Poulenc Rorer Pharmaceuticals, Inc., Collegeville, Pa.

In another aspect, the present invention relates to a method of preventing/treating male impotency with testosterone, osteoporosis with Calcitonin, inhibition of metastasis of tumors with octreotide acetate, suppression of appetite, craving and control of food intake with CCK-8 and analogs, control of drug abuse with methadone and control of yeast infection of HIV patients with mystatin.

In a third aspect, the present invention relates to a process of making a slow, controlled rate release device for releasing a pharmaceutically acceptable active agent into the oral cavity.

In the detailed description which follows, the invention will be described with reference to manufacturing sodium fluoride containing controlled-release devices. The preparation of the devices containing active agents other than sodium fluoride, is analogous to that of sodium fluoride-containing devices and should be readily apparent to those skilled in the art.

DETAILED DESCRIPTION OF THE INVENTION

In the preferred aspect, this invention relates to a manufacturing process for making a sodium fluoride releasing matrix tailor-made to slowly release sodium fluoride at a controlled and predictable rate into the oral cavity to prevent tooth decay and the onset of dentinal root caries, said process comprising the steps of:

preparing a core comprising sodium fluoride and HEMA:MMA copolymer; and coating said core with a membrane forming copolymer of HEMA:MMA.

Preparation of Cores

The fluoride releasing cores are prepared by thoroughly mixing about 1 to 84% w/w, preferably about 74% w/w, of USP grade sodium fluoride and about 35 to 15% w/w, preferably about 25% w/w, of HEMA:MMA copolymer comprising from about 40 mole % to about 60 mole %, HEMA and from about 60 mole % to about 40 mole % MMA, preferably about 50:50 HEMA:MMA in a blender to form a uniform blend of the components. The blend is then granulated by slowly adding a solvent mixture consisting of from about 20% v/v to about 40% v/v and preferably about 30% v/v ethyl acetate and from about 80% v/v to about 60% v/v, preferably about 70% v/v isopropanol, in a suitable mixer to form a granulated paste. The paste is then forced through a 12 mesh (1,700 microns) standard sieve series stainless steel screen to form uniform granules and dried until the solvent odor is undetectable. The dried granules are then sieved through an 18 mesh (1,000 microns) screen. Any residual granules remaining on the screen are reduced to less than 18 mesh by grinding in a centrifugal mill. The granules are then blended with USP talc in a ratio of about 95 to 99 parts granules and about 5 to 1 parts talc. The so-obtained homogeneous mixture is then compressed into the desired shapes, such as tablets, capsules, globules, half-football shapes, veneers or thick films. Compressing is accomplished using a Manesty Beta-tablet press or similar device.

Coating the Cores

In the oral environment the above-described cores would readily release the fluoride content in a relatively short time. Such release of certain oral agents may be desirable, such as an oral anesthetic after oral surgery or for reducing pain due to inflammation of the gums. However, fluoride ions are intended to be released slowly over an extended period of time to prevent coronal and root caries formation. To obtain a product with slow-release characteristics a membrane-forming copolymer-coating is applied onto the cores or matrix.

It was found that the use of HEMA:MMA co-polymer provides a coating that allows for essentially tailor-making the duration and degree of slow release ranging from a couple of weeks or less to several months.

The membrane coating of the cores is accomplished using a fluidized bed processing unit, such as the Glatt fluidized bed processing unit equipped with a Wurster insert, as follows:

generating an upward moving high velocity air stream controlled by an air distribution plate located at the bottom of the coating chamber;

placing a partitioning cylinder (Wurster insert) having a top end and a bottom end over said air distribution cylinder and allowing a gap between the bottom of said cylinder and said air distribution plate;

injecting the cores into said high velocity air stream to propel said cores to move upward and separate from each other;

spraying a solution of 30:70 mole % HEMA:MMA co-polymer in a suitable solvent onto the cores being propelled upward;

maintaining an elevated temperature in the high velocity air stream to vaporize the solvent used to dissolve said HEMA:MMA co-polymer and thereby forming a membrane coating of said co-polymer on said cores;

allowing said coated cores to clear the top of said partitioning cylinder and to fall back on the air distribution plate outside said cylinder;

allowing said cores to move through the gap beneath the partitioning cylinder toward the center of the air distribution plate; and allowing said cores to move upward again in said airstream to be coated again until the desired amount of membrane coating is obtained thereon.

The solution of the membrane forming HEMA:MMA co-polymer should be at a concentration of about 1 to 10% w/w, preferably about 3 to 5% w/w HEMA:MMA in a suitable solvent mixture.

The percentage of coating applied is determined periodically during the coating process as follows:

$$\% \text{ coating} = \frac{\text{mean core wt. after coating} - \text{mean core weight before coating}}{\text{mean coating weight after coating}} \times 100$$

The process continues until the desired membrane coating levels are obtained, typically 14–18% w/w to release a 0.05 to 0.15 mg/day of fluoride. Other rates are obtainable by applying more or less coating on the cores thereby tailor-making the rate of release to the length of time for slow release desired.

The following preferred solvent mixtures are used in the practice of the present invention.

Solvent Mixture A is prepared by mixing
28.50% v/v ethyl acetate with
71.50% v/v isopropyl alcohol Solvent Mixture B is prepared by mixing
80.00% v/v methylene chloride with
20.00% v/v isopropyl alcohol.

The following examples are intended to illustrate the present invention without limitation thereof.

EXAMPLE 1 (GENERAL EXAMPLE)

The desired amounts of powdery ingredients are weighed into separate polyethylene bags and the weights are recorded. The sodium fluoride and the HEMA:MMA 50:50 co-polymer are transferred into a "V" blender and mixed for about five minutes and then discharged into a sigma blender for granulation.

While mixing in the sigma blender, the batch is sprayed with Solvent Mixture A until the batch is sufficiently solvent-wetted for granulation. When the batch is wet enough so that the particles stick together, it is passed through a 12 mesh (1,700 microns) stainless steel sieve and spread on parchment paper lined trays for drying. The larger lumps which did not pass through the sieve are dried separately and, when sufficiently dry, are broken-up with a centrifugal grinder. When dry, the entire batch is sieved through a 20 mesh (850 microns) sieve and collected in a polyethylene container.

Using the desired shape punches and dyes cores are compressed using the Manesty Beta-press machine. The cores are checked every few minutes during the compressing cycle for weight, hardness and thickness. Adjustment on the running weight can be made on the machine, if so desired. The cores are then collected in a polyethylene container.

The Uniglatt coating machine is primed with Solvent Mixture B prior to starting the coating process. The coating process starts by first recording the average weight of the cores. The cores are then placed in the product container of the Uniglatt machine. The unit is sealed by air pressure and the air flap adjusted to the required fluidization. The changes on the Product Exhaust gauge are continuously monitored to ascertain that there is no co-polymer build-up on the exhaust filter. The proportioning pump delivery rate is set to about 1.5, the spray air pressure is set to about 0.5 bar and the spraying of the fluidized cores is started. The build-up of the co-polymer membrane on the cores is checked about every 15 minutes and recorded. When the desired coating level is achieved the proportioning pump and the spray air pressure is shut-off but the fluidizing is continued for about 20 to 30 minutes to drive off the residual solvent.

The finished product is then discharged from the Uniglatt product container into polyethylene storage containers and the net weight is recorded.

Coating weight is calculated by the following equation:

$$\% \text{ coating weight} = \frac{(X - Y) \times 100}{X}$$

where

X=average weight of coated product
Y=average weight of uncoated products.

EXAMPLE 2

Utilizing the procedure described in General Example 1, the following samples were prepared:

| I. Granulation | % W/W |
|---|---|
| Actives* | 1.0–74.25 |
| HEMA:MMA (50:50) | 98.0–24.75 |
| Talc, U.S.P. | 1.00 |
| | 100.00 |

| II. Cores | mg | mg |
|---|---|---|
| Actives* | 38.61 | 1.00 |
| HEMA:MMA (50:50) | 12.87 | 20.48 |
| Talc, U.S.P. | 0.52 | 0.52 |
| | 52.00 | 22.00 |

| III. Coated Cores | mg | % W/W |
|---|---|---|
| Actives* | 38.61 | 61.97 |
| HEMA:MMA (50:50) | 12.87 | 20.66 |
| Talc, U.S.P. | 0.52 | 0.84 |
| HEMA:MMA (30:70) | 10.30 | 16.53 |
| | 62.30 | 100.00 |

| IV. Coated Cores | mg | % W/W |
|---|---|---|
| Actives* | 1.00 | 2.9 |
| HEMA:MMA (50:50) | 20.48 | 60.2 |
| Talc, U.S.P. | 0.52 | 1.5 |
| HEMA:MMA (20:80) | 12.00 | 35.4 |
| | 34.00 | 100.00 |

*Actives are: testosterone, calcitonin, octreotide acetate, CCK, CCK-analogs, methadone and nystatin.

EXAMPLE 3

| I. Granulation | % W/W | 2 Kilo Batch (g) |
|---|---|---|
| Sodium fluoride, U.S.P. | 74.25 | 1485.00 |
| HEMA:MMA (50:50) | 24.75 | 495.00 |
| Talc, U.S.P. | 1.00 | 20.00 |
| | 100.00 | 2000.00 |

| II. Cores | mg | mg |
|---|---|---|
| Sodium fluoride, U.S.P. | 61.63 | 38.61 |
| HEMA:MMA (50:50) | 20.54 | 12.87 |
| Talc, U.S.P. | 0.83 | 0.52 |
| | 83.00 | 52.00 |

| III. Coated Cores | mg | % W/W | mg | % W/W |
|---|---|---|---|---|
| Sodium fluoride, U.S.P. | 61.63 | 62.25 | 38.61 | 61.97 |
| HEMA:MMA (50:50) | 20.54 | 20.75 | 12.87 | 20.66 |
| Talc, U.S.P. | 0.83 | 0.84 | 0.52 | 0.84 |
| HEMA:MMA (30:70) | 16.00 | 16.16 | 10.30 | 16.53 |
| | 99.00 | 100.00 | 62.30 | 100.00 |

EXAMPLE 4

The rate of fluoride-release from HEMA:MMA membrane coated sodium fluoride core tablets was evaluated. The tablets consisted of a sodium fluoride containing core coated with a rate-controlling co-polymer membrane. Four samples with varying polymer coating thickness were studied.

The composition of the final 14% co-polymer coated tablet is:

| Core | Sodium Fluoride | 55.99 mg |
|---|---|---|
| | HEMA:MMA (50:50 mole %) | 18.66 |
| | Talc | 0.75 |
| Coating | HEMA:MMA (30:70 mole %) | 12.80 |
| | TOTAL | 88.20 mg |

The specification of the 14% co-polymer coated tablet is:

| NaF Content | 55.99 NaF-25.33 mg F-ion |
|---|---|
| Dimensions in mm | 8.4(l) × 3.4(w) × 2.4(h) |
| Average Weight | 88.1 ± 0.5 mg |
| F-ion Release | 0.09 mg per 24 hours |

The core preparation consisted of mixing the 50:50 mole % HEMA:MMA co-polymer with sodium fluoride in a blender. The mixture was granulated to a paste, passed through a sieve to obtain granules. The granules were dried in an oven under a stream of warm and dry air, not exceeding 80° C. and 40% humidity, until all solvents were removed. If residual solvent odor was detected, the granules were dried in a desiccator under vacuum. The granules were reduced in size using a centrifugal grinding mill, and compressed into cores of desired shape.

The release rate-controlling membrane was applied by the method described in Example 1. The coating was composed of 30:70 mole % HEMA:MMA co-polymer and it was applied in four steps. The rate of fluoride release was determined after each coating step.

Standard Test Method

Fluoride release rates from the intraoral fluoride-releasing device (IFRD) were determined as follows:

1. Scope and Purpose
  1.1 This method used to determine the average daily fluoride ($F^-$) release rate from intraoral fluoride-releasing devices (IFRD) designed to passively release controlled (constant) amounts of $F^-$ into the oral cavity for at least six months.

2. Principle of Method
  2.1 An IFRD is placed in a plastic jar and a diffusion buffer solution is added. The jar is mounted in a rotator and the entire apparatus is placed in a thermostated incubator. The diffusion buffer simulates the pH and ionic strength of saliva and contains the major salivary ions (except calcium). The amount of $F^-$ released by the IFRD into the diffusion buffer is assayed potentiometrically with a $F^-$ ion specific electrode and an Orion® 940 Expandable Ion Analyzer or equivalent electrometer.

3. Interferences
  3.1 Due to the inherent reactivity of $F^-$ ion with glass, all $F^-$ solutions were mixed, stored and dispensed from plastic labware.
  3.2 Ionic activity is a function of temperature. Whenever laboratory temperature varied by more than 2° C. from the original standardization conditions, standardization was repeated.
  3.3 Since the $F^-$ ion specific electrode responds to hydroxide ($OH^-$) ion, but does not respond to HF, all $F^-$ measurements were carried out in between pH 5.0 to 5.5 to minimize erroneously high readings due to $OH^-$ ion contribution or to the formation of HF [$Ka_{(HF)}=3.5\cdot10^{-3}$].
  3.4 A total ionic strength adjusting buffer (TISAB-II) Orion® was used in equal proportions with all $F^-$ solutions to provide a constant background ionic strength, to decomplex bound $F^-$ and to adjust solution pH between 5.0 and 5.5.

4. Precision and Accuracy
  4.1 Precision: Measured concentration of $F^-$ is reproducible to ±2% based on repeated (n=10) measurements of one sample.
  4.2 Accuracy: Based on repeated (n=10) measurements of a 5.0 ppm $F^-$ standard solution, the accuracy is ±4%.

5. Reagents
  5.1 Orion® TISAB-II (#940909).
  5.2 Orion® 100±0.5 ppm $F^-$ standard solution (#940907).
  5.3 Orion® 1 ppm $F^-$/TISAB standard solution (#040906).
  5.4 Orion® 10 ppm $F^-$/TISAB standard solution (#040908).
  5.5 Baxter® pH 7.00 calibrating buffer solution (#H7590-7A) or equivalent.
  5.6 Baxter® pH 4.00 calibrating buffer solution (#H7590-7A) or equivalent.
  5.7 Deionized distilled water (DDW)
  5.8 Diffusion buffer stock solution:
    5.8.1 Solution A: dissolve 1.24 g $NaH_2PO_4\cdot H_2O$, 115.13 g KCl and 2.0 g $NaN_3$ in 600 ml DDW.
    5.8.2 Solution B: dissolve 41.98 g 3-(4-morpholino)-propane sulfonic acid [MOPS] in 300 ml water.
    5.8.3 Solution B is added to Solution A and pH is adjusted to 7.3 using 50% NaOH (ca. 10 mls). Sufficient water is added to make 1 L.
  5.9 Diffusion buffer solution: Prior to use, diffusion buffer stock solution is diluted [5.8.3.] 10-fold (100 ml stock solution diluted with 900 ml DDW) and pH adjusted to 7.0 if required. The diffusion buffer system has a $pK_a$ 7.2 with $\Delta pH/°C.=-0.006$) and is bactericidal.

6. Standardization
  6.1 Unit Performance Check: according to Orion® manufacturer's manual.
  6.2 pH Calibration: according to manufacturer's manual. A two-point calibration with pH 4.00 and 7.00 standard buffers is used.
  6.3 $F^-$ Calibration: according to Orion® manufacturer's manual. A two-point calibration with 1.00 ppm $F^-$ and 10.0 ppm $F^-$ standard solutions is used.

7. Procedure
  7.1 IFRD Selection/Inspection: Devices are randomly selected and visually inspected under 10× magnification for defects (obvious cracks or other membrane imperfections) until six satisfactory devices are obtained.
  7.2 IFRD $F^-$ Release: Each inspected device is weighed to the nearest 0.1 mg and placed individually into a 120 ml plastic jar which was pre-rinsed with diffusion buffer solution. Jar and lid are labelled with an identifying number. 100 ml of diffusion buffer [5.9.] is added to each jar. Each jar is mounted on the platter of an end-over-end rotator (Fischer Scientific Chemistry Mixer) at using two large rubber bands and the rotator is placed into a thermostated incubator.
  7.3 Diffusion Buffer Blank: A diffusion buffer blank jar to correct for the background amount of $F^-$ was prepared by adding 100 ml of diffusion buffer [5.9] to a jar without an IFRD. This jar was mounted with the IFRD sample jars [7.2.].
  7.4 IFRD Buffer Change: Jars [7.2., 7.3.] from the incubator were removed on each Monday and Friday and a 10 ml aliquot of each buffer solution was decanted into separate, prelabeled 15 ml plastic tubes for subsequent $F^-$ analysis. The remainder of the diffusion buffer was discarded. 100 ml of fresh diffusion buffer [5.9.] was added to all jars and replaced in the incubator. The diffusion buffer changes were repeated until the $F^-$ release had ceased. Date and time of buffer change were recorded to nearest half hour and rotation (8 rpm) was continued.
  7.5 $F^-$ measurements: 2.0 ml of each diffusion buffer aliquot [7.4.] was transferred into a 30 ml plastic cup and 2.0 ml of TISAB solution was added. A magnetic stirring bar was inserted and stirred gently. A previously standardized $F^-$ ion specific electrode was placed into the stirred sample and the $F^-$ concentration (ppm) was measured to the nearest 0.01 ppm $F^-$. When the meter reading was stable, the $F^-$ concentration was recorded. The electrode was rinsed with distilled water and blotted dry with a soft tissue. If the laboratory temperature varied by more than 2° C. from original standardization conditions, the $F^-$ electrode was re-standardized.

8. Calculations
  8.1 The total amount (mg) of $F^-$ contained within each jar was calculated by multiplying the meter reading (ppm $F^{31}$) of each sample aliquot [7.2.] by the volume of diffusion buffer in liters (L). [ppm=mg $F^-$/L]
  8.2 The net amount (mg) of $F^-$ released from the IFRD into the diffusion buffer was calculated by subtracting the background amount of $F^-$ from the total amount of $F^-$ present in each sample of diffusion buffer.
  8.3 The average daily $F^-$ release rate was calculated as the net amount of $F^-$ released (mg) into the buffer divided by the number of elapsed days between buffer changes. (Rate=mg $F^-$/day).

The fluoride-release rates were found to be proportional to the thickness of the rate-controlling co-polymer membrane. The theoretical release rates and actual results are as follows:

| Coating | Theoretical F- Release/ 24 hr | Theo. Total Release Time | Actual Release 24/hr | Actual F- Release Time | % F Released |
| --- | --- | --- | --- | --- | --- |
| 8% | 0.3 mg | 84 days | 0.27 mg | 86 days | 100 |
| 10% | 0.15 mg | 168 days | 0.135 mg | 164 days | 89 |
| 14% | 0.09 mg | 282 days | 0.10 mg | 260 days | 96 |
| 18% | 0.075 mg | 308 days | 0.07 mg | 320 days | 97 |

EXAMPLE 5 (Comparative Example based on U.S. Pat. No. 4,919,939)

Microspheres were prepared as follows:

Hydrogel particles of methyl methacrylate (MMA) and hydroxyethyl methacrylate (HEMA) containing micronized sodium fluoride were prepared by: dissolving 3 g of the HEMA/MMA co-polymer in a mixture of 25 ml of 60:40 acetone: p-dioxane; suspending 1.0 g of micronized sodium fluoride in the solution; casting a 200 micron thin film onto a glass plate; and drying the film.

Three kinds of samples were prepared from the film:

a) the film as is;

b) the film was ground into particles with an average diameter of 100–200 microns; and c) the ground film particles were formed into tablets.

The three kinds of samples were tested for fluoride release as described in the Standard Test Method.

The results showed that:

a) the film samples released most of their fluoride content in about 12 to 13 hours;

b) the ground-up film samples released most of their fluoride content in about 9 to 10 hours; and c) the tableted film samples released most of their fluoride content in about 14 to 15 hours.

EXAMPLE 6

Fluoride release was tested utilizing 14% HEMA/MMA coated NaF tablets of the present invention using the Standard Test Methods. Two sets of samples were tested.

a) One set of samples were immersed in water in beakers, these are the so-called "Unattached" samples, unhindered by any attachment to teeth and all the surfaces of the samples are available for fluoride release.

b) The other set of samples were mounted onto teeth, i.e. "Attached", simulating the actual environment in use in the patients' mouths.

The result showed that:

a) the "Unattached" samples released most of their fluoride content in about 120 to 140 days; and b) the "Attached" samples released most of their fluoride content in about 260 to 270 days.

Those skilled in the art will appreciate that other drugs, flavors and pharmaceutically acceptable mouth deodorants in the form of solids or liquids may be incorporated into the slow release device of the present invention. Their rate of release and amount of release can be tailor-made as illustrated in Example 3.

The present invention is also directed to a method of preventing dental caries (enamel and dentinal), development of incipient carious lesions (white spot lesions) around orthodontic appliances in the oral cavity in a mammal by administering an effective amount of $F^-$ to said mammal that is released at a constant rate from the slow, controlled rate-release device which is placed into the oral cavity. Such release should be from about 0.01 to about 0.15 mg/day of $F^-$ from about 80 to about 2530 days.

The invention also provides a method of treating periodontal diseases in a mammal by inhibiting collagenolytic enzyme by releasing from a slow, controlled rate-release device, which is placed into the oral cavity, a collagenolytic enzyme inhibitor at a rate of from about 0.05 to about 1.0 mg/day for 30 to 180 days.

Those skilled in the art of prevention/treatment of dental diseases will appreciate the significance of the above-referred two methods.

As referred to earlier, dental caries is a prevalent disease affecting almost all adults. Caries in patients whose salivary flow has been reduced pose special risks. Radiation therapy to the head and neck for treatment of cancer results in a marked decrease in salivation when the field of radiation includes the major salivary glands. Those with resultant xerostomia can experience a rampant caries rate of 2.5 surfaces per month. If these teeth become badly infected with caries and have to be extracted, the patient is also at risk for osteoradionecrosis, a sometimes fatal disease.

Fluorides have been documented to be effective in reducing caries. Low concentrations of fluoride compounds are provided in water, dentifrices, and mouth rinses. Professionally applied highly concentrated fluoride preparations are available in the dentist's office. For patients with active caries, high concentration home-use fluorides are available by prescription. These home use fluorides have also been shown to prevent caries in xerostomic populations. The typical treatment recommended is to provide the patient with custom made trays. The patient then self-administers approximately 5 ml of a 1.1% NaF (prescription) for 4 minutes daily. This method is cumbersome, messy, can cause gagging and needs 100% compliance on the part of the patient in order to be effective in preventing caries.

There is also concern that daily use of a high fluoride concentration can result in inadvertent ingestion of high doses of $F^-$ that causes fluoride toxicity and the development of gastric ulcers.

Low levels of fluoride work in preventing caries by facilitating the remineralization process while a tooth is exposed to a caries attack. The method of the present invention delivers a daily low dose of fluoride without the problems of complying with a cumbersome regime.

An Intraoral Fluoride Releasing System (IFRS) consisting of a retainer containing a slow-releasing sodium fluoride pellet (IFRD), provides a constant, low level (0.07 mg daily) source of fluoride. After installation of the $F^-$ releasing device into the oral cavity by a dentist, the device releases fluoride automatically and requires no compliance on the part of the patient. These patients will be wearing two IFRD's and, therefore, will be receiving 0.14 mg $F^-$ daily (or 0.31 mg as NaF). There is an abundance of data to show that 0.14 mg $F^-$ daily is non-toxic and non-irritating.

It will also be understood that while the preferred embodiment of the invention has been described, variations may be made thereto without departing from the spirit of the invention.

What is claimed is:

1. A controlled rate-release device for attachment to teeth in the oral cavity capable of releasing a pharmaceutically active agent at a constant rate comprising:

(a) a plurality of discrete granules being in the particle size range of from about 850 to about 1,700 microns and consisting essentially of (1) of from about 1 to about 84% w/w of a pharmaceutically active agent in finely divided power form imbedded in a solid non-erodable co-polymeric structure of (2) 35 to about 15% w/w of 2-hydroxyethyl methacrylate/methyl methacrylate copolymer which comprises from about 40 to about 60 mole % of 2-hydroxyethyl methacrylate and from about 60 to about 40% mole of methyl methacrylate, wherein in each of said granules said co-polymeric structure surrounds the finely divided particles of said pharmaceutically acceptable active agent, and wherein said granules are compressed into dosage forms in the shape of tablets, capsules, globules, half-football shapes, veneers or thick films and are coated with (b) a non-erodable diffusion rate-controlling membrane consisting essentially of from about 20 to about 40 mole % of 2-hydroxyethyl methacrylate and from about 60 to about 80 mole % of methyl methacrylate.

2. The controlled rate-release device of claim 1 wherein said pharmaceutically acceptable active agent is selected from the group consisting of an antibiotic, an antimicrobial, a salivary stimulant and a mouth deodorant.

3. The controlled rate-release device of claim 2 wherein said antibiotic is tetracycline.

4. The controlled rate-delivery device of claim 3 wherein said tetracycline is selected from the group consisting of doxycycline, minocycline, 4,4-dedimethylamino-tetracycline; 4-hydroxy-4-dedimethylamine tetracycline, tetracycline-2-hydroxamate and other chemically modified non-antimicrobial tetracycline.

5. The controlled rate-release device of claim 2 wherein said antimicrobial is selected from the group consisting of cetylpyridinium, chlorhexidine and metronidazole.

6. The controlled rate-release device of claim 2 wherein said salivary stimulant is pilocarpin.

7. The controlled rate release device of claim 2 wherein said mouth deodorant is alpha or beta ionone.

8. The controlled rate-release device of claim 1 wherein said pharmaceutically active agent is a fluoride ion-releasing substance selected from the group consisting of calcium fluoride, amine fluoride, sodium monofluorophosphate and stannous fluoride.

9. The controlled rate-release device of claim 1 wherein said pharmaceutically active agent is selected from the group consisting of: testerone, calcitonin, octreotide acetate, cholecystokinin, C-terminal octapeptide of cholecystokinin, derivatives of cholecystokinin, methadone hydrochloride and nystatin.

10. The controlled rate release device of claim 1 wherein said rate controlling co-polymer comprises about a 30:70 mix of 2-hydroxyethyl methacrylate and methyl methacrylate.

11. A method of preventing dental caries development in a mammal by administering an effective amount of $F^-$ to said mammal that is released at a constant rate from a controlled rate-release device capable of releasing said $F^-$ into the oral cavity, said controlled rate-release device comprising:

(a) a plurality of discrete granules being in the particle size range of from about 850 to about 1,700 microns and consisting essentially of (1) of from about 1 to about 84% w/w of a $F^-$ containing agent in finely divided power form imbedded in a solid non-erodable co-polymeric structure of from 35 to about 15% w/w of 2-hydroxyethyl methacrylate/methyl methacrylate co-polymer which comprises from about 40 to about 60 mole % of 2-hydroxyethyl methacrylate and from about 60 to about 40 mole % of methyl methacrylate wherein in each of said granules said co-polymeric structure surrounds the finely divided particles of said $F^-$ containing agent, and wherein said granules are compressed into dosage forms in the shape of tablets, capsules, globules, half-football shapes, veneers or thick films and are coated with (b) a non-erodable rate-controlling co-polymer membrane consisting essentially of from about 20 to about 40 mole % of 2-hydroxyethyl methacrylate and from about 60 to about 80 mole % of methyl methacrylate.

12. A method of preventing/treating incipient carious lesions around orthodontic appliances by providing an effective amount of $F^-$ that is released at a constant rate from a controlled rate-release device installed into the oral cavity, said controlled rate-release device capable of releasing said $F^-$ into the oral cavity, said controlled rate-release device comprising:

(a) a plurality of discrete granules being in the particle size range of from about 850 to about 1,700 microns and consisting essentially of (1) from about 1 to about 84% w/w of said $F-$ containing agent in finely divided power form imbedded in a solid non-erodable co-polymeric structure of from about 35 to about 15% w/w of 2-hydroxyethyl methacrylate/methyl methacrylate co-polymer which comprises from about 40 to about 60 mole % of 2-hydroxyethyl methacrylate and from about 60 to about 40 mole % of methyl methacrylate wherein in each of said granules said co-polymeric structure surrounds the finely divided particles of said $F^-$ containing agent, and wherein said granules are compressed into dosage forms in the shape of tablets, capsules, globules, half-football shapes, veneers or thick films and are coated with (b) a non-erodable rate-controlling co-polymer membrane consisting essentially of from about 20 to about 40 mole % of 2-hydroxyethyl methacrylate and from about 60 to about 80 mole % of methyl methacrylate.

13. The method of claim 11 wherein form about 0.01 to about 0.15 mg/day of $F-$ is constantly released from said device into the oral cavity from 90 to 265 days.

14. The method of claim 12 wherein from about 0.01 to about 0.15 mg/day of $F-$ is constantly released from said device into the oral cavity from 90 to 265 days.

15. A method of preventing periodontal disease in a mammal by administering an effective amount of a collagenolytic enzyme inhibitor to said mammal that is released at a constant rate from a controlled rate-release device capable of releasing said collagenolytic enzyme inhibitor into the oral cavity, said controlled rate-release device comprising (a) a plurality of discrete granules being in the particle size range of from about 850 to about 1,700 microns and consisting essentially of (1) from about 1 to about 84% w/w of said collagenolytic enzyme inhibitor in finely divided power form imbedded in a solid non-erodable co-polymeric structure of from about 35 to about 15% w/w of 2-hydroxyethyl methacrylate/methyl methacrylate co-polymer which comprises from about 40 to about 60 mole % of 2-hydroxyethyl methacrylate and from about 60 to about 40 mole % of methyl methacrylate wherein in each of said granules said co-polymeric structure surrounds the finely divided particles of said collagenolytic enzyme inhibitor, and wherein said granules are compressed into dosage forms in the shape of tablets, capsules, globules, half-football shapes, veneers or thick films and are coated with (b) a non-erodable rate-controlling co-polymer membrane consisting essentially of from about 20 to about 40 mole % of 2-hydroxyethyl methacrylate and from about 60 to about 80 mole % of methyl methacrylate.

16. The method of claim 15 wherein from about 0.05 to about 1.0 mg/day of a collagenolytic enzyme inhibitor is released constantly from the controlled release device into the saliva for 30 to 360 days.

17. The method of claim 16 wherein the collagenolytic enzyme inhibitor is selected from the group consisting of doxycycline, minocycline, 4,4-dedimethylamino-tetracycline, 4-hydroxy-4,4-dedimethylaminotetracycline and tetracycline-2-hydroxamate.

18. A method of treating testosterone deficiency in a mammal by administering an effective amount of testosterone that is released at a constant rate from a controlled rate-release device capable of releasing said testosterone into the oral cavity, said controlled rate-release device comprising:

(a) a plurality of discrete granules being in the particle size range of from about 850 to about 1,700 microns and consisting essentially of
   (1) from about 1 to about 84% w/w of said testosterone in finely divided power form imbedded in a solid non-eroable co-polymeric structure of from about 35 to about 15% w/w of 2-hydroxyethyl methacrylate/ methyl methacrylate co-polymer which comprises from about 40 to about 60 mole % of 2-hydroxyethyl methacrylate and from about 60 to about 40 mole % of methyl methacrylate wherein in each of said granules said co-polymeric structure surrounds the finely divided particles of said testosterone, and wherein said granules are compressed into dosage forms in the shape of tablets, capsules, globules, half-football shapes, veneers or thick films and are coated with (b) a non-erodable rate-controlling co-polymer membrane consisting essentially of from about 20 to about 40 mole % of 2-hydroxyethyl methacrylate and from about 60 to about 80 mole % of methyl methacrylate.

19. A method of treating osteoporosis deficiency in a mammal by administering an effective amount of calcitonin that is released at a constant rate from a controlled rate-release device capable of releasing said calcitonin into the oral cavity, said controlled rate-release device comprising:

(a) plurality of discrete granules being in the particle size range of from about 850 to about 1,700 microns and consisting essentially of
   (1) from about 1 to about 84% w/w of said calcitonin in finely divided power form imbedded in a solid non-erodable co-polymeric structure of from about 35 to about 15% w/w of 2-hydroxyethyl methacrylate/methyl methacrylate co-polymer which comprises from about 40 to about 60 mole % of 2-hydroxyethyl methacrylate and from about 60 to about 40 mole % of methyl methacrylate wherein in each of said granules said co-polymeric structure surrounds the finely divided particles of said calcitonin, and wherein said granules are compressed into dosage forms in the shape of tablets, capsules, globules, half-football shapes, veneers or thick films and are coated with (b) a non-erodable rate-controlling co-polymer membrane consisting essentially of from about 20 to about 40 mole % of 2-hydroxyethyl methacrylate and from about 60 to about 80 mole % of methyl methacrylate.

20. A method of suppressing appetite in a mammal by administering an effective amount of cholecystokinin that is released at a constant rate from a controlled rate-release device capable of releasing said cholecystokinin into the oral cavity, said controlled rate-release device comprising:

(a) a plurality of discrete granules being in the particle size range of from about 850 to about 1,700 microns and consisting essentially of
   (1) from about 1 to about 84% w/w of said cholecystokinin in finely divided power form imbedded in a solid non-erodable co-polymeric structure of from about 35 to about 15% w/w of 2-hydroxyethyl methacrylate/methyl methacrylate co-polymer which comprises from about 40 to about 60 mole % of 2-hydroxyethyl methacrylate and from about 60 to about 40 mole % of methyl methacrylate wherein in each of said granules said co-polymeric structure surrounds the finely divided particles of said cholecystokinin, and wherein said granules are compressed into dosage forms in the shape of tablets, capsules, globules, half-football shapes, veneers or thick films and are coated with (b) a non-erodable rate-controlling co-polymer membrane consisting essentially of from about 20 to about 40 mole % of 2-hydroxyethyl methacrylate and from about 60 to about 80 mole % of methyl methacrylate.

21. A method of suppressing craving for drugs in a mammal by administering an effective amount of methodone hydrochloride that is released at a constant rate from a controlled rate-release device capable of releasing said methodone hydrochloride into the oral cavity, said controlled rate-release device comprising:

(a) a plurality of discrete granules being in the particle size range of from about 850 to about 1,700 microns and consisting essentially of
   (1) from about 1 to about 84% w/w of said methodone hydrochloride in finely divided power form imbedded in a solid non-erodable co-polymeric structure of from about 35 to about 15% w/w of 2-hydroxyethyl methacrylate/methyl methacrylate co-polymer which comprises from about 40 to about 60 mole % of 2-hydroxyethyl methacrylate and from about 60 to about 40 mole % of methyl methacrylate wherein in each of said granules said co-polymeric structure surrounds the finely divided particles of said methodone hydrochloride, and wherein said granules are compressed into dosage forms in the shape of tablets, capsules, globules, half-football shapes, veneers or thick films and are coated with (b) a non-erodable rate-controlling co-polymer membrane consisting essentially of from about 20 to about 40 mole % of 2-hydroxyethyl methacrylate and from about 60 to about 80 mole % of methyl methacrylate.

22. A method of treating yeast infection in a mammal by administering an effective amount of nystatin that is released at a constant rate from a controlled rate-release device capable of releasing said nystatin into the oral cavity, said controlled rate-release device comprising:

(a) a plurality of discrete granules being in the particle size range of from about 850 to about 1,700 microns and consisting essentially of
   (1) from about 1 to about 84% w/w of said nystatin in finely divided power form imbedded in a solid non-erodable co-polymeric structure of from about 35 to about 15% w/w of 2-hydroxyethyl methacrylate/methyl methacrylate co-polymer which comprises from about 40 to about 60 mole % of 2-hydroxyethyl methacrylate and from about 60 to about 40 mole % of methyl methacrylate wherein in each of said granules said co-polymeric structure surrounds the finely divided particles of said nystatin, and wherein said granules are compressed into dosage forms in the shape of tablets, capsules, globules, half-football shapes, veneers or thick films and are coated with (b) a non-erodable rate-controlling co-polymer membrane consisting essentially of from about 20 to about 40 mole % of 2-hydroxyethyl methacrylate and from about 60 to about 80 mole % of methyl methacrylate.

23. A method of inhibiting metastasis of tumors in a mammal by administering an effective amount of octreotide acetate that is released at a constant rate from a controlled rate-release device capable of releasing said octreotide acetate into the oral cavity, said controlled rate-release device comprising:

(a) a plurality of discrete granules being in the particle size range of from about 850 to about 1,700 microns and consisting essentially of (1) from about 1 to about 84% w/w of said octreotide acetate in finely divided power form imbedded in a solid non-erodable co-polymeric structure of from about 35 to about 15% w/w of 2-hydroxyethyl methacrylate/methyl methacrylate co-polymer which comprises from about 40 to about 60 mole % of 2-hydroxyethyl methacrylate and from about 60 to about 40 mole % of methyl methacrylate wherein in each of said granules said co-polymeric structure surrounds the finely divided particles of said octreotide acetate, and wherein said granules are compressed into dosage forms in the shape of tablets, capsules, globules, half-football shapes, veneers or thick films and are coated with (b) a non-erodable rate-controlling co-polymer membrane consisting essentially of from about 20 to about 40 mole % of 2-hydroxyethyl methacrylate and from about 60 to about 80 mole % of methyl methacrylate.

* * * * *